(12) United States Patent
Takahashi et al.

(10) Patent No.: US 8,022,295 B2
(45) Date of Patent: Sep. 20, 2011

(54) PHOTOELECTRIC CONVERSION DEVICES

(75) Inventors: Tamotsu Takahashi, Hokkaido (JP); Kiyoshi Musha, Tokyo (JP)

(73) Assignees: Japan Science and Technology Agency, Saitama (JP); Adeka Corporation, Tokyo (JP)

( * ) Notice: Subject to any disclaimer, the term of this patent is extended or adjusted under 35 U.S.C. 154(b) by 0 days.

(21) Appl. No.: 12/772,800

(22) Filed: May 3, 2010

(65) Prior Publication Data

US 2010/0206382 A1    Aug. 19, 2010

Related U.S. Application Data

(62) Division of application No. 11/628,155, filed as application No. PCT/JP2005/009933 on May 31, 2005, now abandoned.

(30) Foreign Application Priority Data

Jun. 1, 2004    (JP) .................. 2004-163714

(51) Int. Cl.
*H01L 51/42* (2006.01)
*H01L 31/04* (2006.01)

(52) U.S. Cl. ...................................... 136/263

(58) Field of Classification Search ........... 136/243–265
See application file for complete search history.

(56) References Cited

U.S. PATENT DOCUMENTS

| | | | |
|---|---|---|---|
| 6,340,789 B1 | 1/2002 | Petritsch et al. | |
| 6,352,777 B1 | 3/2002 | Bulovic et al. | |
| 6,690,029 B1 | 2/2004 | Anthony et al. | |
| 2005/0240061 A1 | 10/2005 | Takahashi et al. | |
| 2007/0102696 A1* | 5/2007 | Brown et al. ............... | 257/40 |

FOREIGN PATENT DOCUMENTS

| | | |
|---|---|---|
| EP | 1 416 069 | 5/2004 |
| EP | 1 493 796 | 1/2005 |
| JP | 2003-277742 | 10/2003 |
| KR | 2004-0029402 | 4/2004 |
| WO | WO 03/016599 | 2/2003 |
| WO | 03/080762 | 10/2003 |

OTHER PUBLICATIONS

R.O. Loutfy, et al., "Photovoltaic properties of metal-free phtalocyanines.I.A1/H2Pc Schottky barrier solar cells", Journal of Chemical Physics, 1979, vol. 71, No. 3, pp. 1211 to 1217.

C.W. Tang, "Two-layer organic photovoltaic cell", Applied Physics Letters, 1986, vol. 48, No. 2, pp. 183 to 185.
B.O'Regen, et al., "A low-cost, high-efficiency solar cell based on dye-sensitized colloidal TiO2 films", Nature, 1991, vol. 353, pp. 737 to 740.
K. Murakoshi, et al., "Solid State Dye-sensitized TiO2 Solar Cell with Polypyrrole as Hole Transport Layer", Chemistry Letters, 1997, vol. 26, No. 5, pp. 471 to 472.
Signerski R et al.:, "Photoelectric Properties of Heterojunctions Formed From Di-(Pyridyl)-Perylenetetracarboxlic Diimide and Copper Phthalocyanine or Pentacene" Synthetic Metals, Elsevier Sequoia, Lausanne, CH vol. 94, No. 1, Apr. 15, 1998, pp. 135-137, XP001191068.
Senadeera G K R et al.:, "Solid-state dye-sensitized photocell based on pentacene as a hole collector", Solar Engert Materials and Solar Cells, Elsevier Science Publishers, Amsterdam, NL, vol. 73, No. 1, May 1, 2002 pp. 103-108, XP004348867.
Schoen J H et al., "Efficient Organic Photovoltaic Diodes Based on Doped Pentacene", Nature, Nature Publisihing Group, London, UK vol. 403, No. 6768, Jan. 27, 2000, pp. 408-410, XP000992734.
European Patent Office issued an European Search Report dated Mar. 18, 2010, Application No. 05745890.3.
Japanese Notice of Rejection dated May 10, 2011 in corresponding Japanese Application No. 2006-514095 with English translation of Notice of Rejection.

\* cited by examiner

*Primary Examiner* — Jessica L Ward
*Assistant Examiner* — Kevin E Yoon
(74) *Attorney, Agent, or Firm* — Young & Thompson

(57) ABSTRACT

Materials for photoelectric conversion devices, consisting of polyacene derivatives represented by general formula (I) below; and photoelectric conversion devices made by using the materials. The materials for photoelectric conversion devices have excellent workability and productivity, exhibit low toxicity, are easily flexibilized, and have high photoelectric conversion efficiencies.

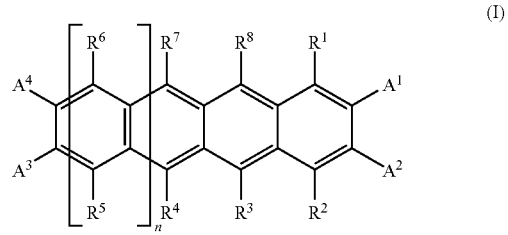

In the formula, $R^1, R^2, R^3, R^4, R^5, R^6, R^7, R^8, A^1, A^2, A^3$, and $A^4$ are independent from each other, either the same or different, and each represents a hydrogen atom, a halogen atom, an optionally substituted hydrocarbon group having 1 to 40 carbon atoms, or the like. n is an integer of 1 or more.

3 Claims, No Drawings

PHOTOELECTRIC CONVERSION DEVICES

The present application is a division of application Ser. No. 11/628,155 filed Nov. 30, 2006, now abandoned

TECHNICAL FIELD

The present invention relates to materials for photoelectric conversion devices that generate electromotive force upon photoirradiation and photoelectric conversion devices using said materials.

BACKGROUND ART

Recently, global warming caused by burning fossil fuel and increase in energy demand associated with population growth have been serious problems influencing existence of human being. Needless to say, sunlight has fostered terrestrial environment and supplied energy to all the living things including human being since ancient times. Thus, recently it has been considered to utilize sunlight as an energy source that is infinitely available and clean without emission of any harmful substances. In particular, attention has been paid to photoelectric devices converting light energy to electric energy, so-called solar cells, as a powerful technology.

As materials for generating electromotive force in solar cells, there have been used silicon in a single crystalline, polycrystalline, or amorphous form and inorganic semiconductors composed of compounds such as CuInSe, GaAs and CdS. Solar cells using these inorganic semiconductors attain relatively high energy conversion efficiencies, 10% to 20%, and therefore they are widely utilized as remote power supplies and auxiliary power supplies in portable small-sized electronic apparatuses. In light of the purpose mentioned in the beginning, namely, for preventing damage to the global environment by reducing consumption of fossil fuel, however, solar cells using inorganic semiconductors cannot be regarded to be sufficiently effective at the present stage. This is because such solar cells using inorganic semiconductors are produced by a plasma-assisted CVD method or a high-temperature crystal growth process, which means that a large quantity of energy is required to produce the devices. Further, such devices contain Cd, As, Se or the like, which possibly have harmful effects on the environment, causing possibility of environmental damages on disposal of the devices.

There have been proposed organic solar cells in which organic semiconductors are used as photovoltaic materials capable of improving the above issue. Organic semiconductors have excellent characteristics: a wide variety of materials are available; toxicity is low; production cost cutting is possible due to high workability and productivity; and they can be readily flexibilized due to the flexing nature; and others. For this reason, organic solar cells have been actively studied toward commercialization.

Organic solar cells are largely classified into semiconductor type and dye-sensitized type. The semiconductor type is classified into two classes, Schottky barrier type and pn junction type, according to the mechanism in dissociation of photo-generated charged pairs. Schottky barrier solar cells utilize internal electric field due to Schottky barrier induced in a junction plane between an organic semiconductor and a metal (see Non-patent Document 1). While such Schottky barrier solar cells can attain relatively high open-circuit voltage (Voc), they have a drawback that the photoelectric conversion efficiencies tend to decrease with an increase in irradiation light intensity. Further, production of Schottky barrier solar cells is generally rather difficult since thin films are required to be formed by various kinds of vapor deposition methods.

The pn junction solar cell, which utilizes internal electric field generated in a junction plane between a p-type semiconductor and an n-type semiconductor, include organic/organic pn junction type, in which organic materials are used for the both semiconductors, organic/inorganic pn junction type, in which an inorganic material is used for either of the semiconductors, and others. The conversion efficiencies of such pn junction solar cells are relatively high but not sufficient (see Non-patent Document 2). In many cases, it is also required to form films by vapor deposition methods as in the case of Schottky barrier solar cells, which impedes improvement of productivity.

On the other hand, in 1991, Gratzel et al. in Switzerland reported a dye-sensitized solar cell using a thin film of porous titanium dioxide with large surface area containing ruthenium bipyridinecarboxylic acid dye adsorbed on a surface thereof as an electrode, and this report attracted great attention (see Non-patent Document 3). However, a problem was pointed out for the use of an electrolytic solution and iodine, and commercialization has been hard to progress. Solidification of the electrolytic solution component could evidently make a significant advance toward commercialization. Although various methods have been tried for the solidification, the photoelectric conversion efficiencies of such systems are still lower than those of wet-type solar cells using electrolytic solutions. For example, conductive polymers such as polyaniline, polypyrrole, polythiophene, and the like, have been examined, but the conversion efficiency is low in any case (see Non-patent Document 4). For such a solidification method of replacing the electrolytic solution component by a p-type semiconductor layer working as a hole-transporting layer, there may be pointed out structural similarity to a pn junction solar cell except that the n-type semiconductor electrode is a porous material and that an organic dye layer is provided.

Furthermore, it is known that organic semiconducting compounds considered to be valuable for solar cells exhibit different properties, for example, photoelectric characteristics (electromotive characteristics), depending on crystal forms, and that only specific crystal forms exhibit excellent photoelectric characteristics. To selectively generate a crystal form in a film forming step by a vapor deposition method, improvement has been attempted by controlling the substrate temperature, but it is difficult to obtain a semiconductor layer in the desired crystal form having good photoelectric characteristics.

Non-patent Document 1: R. O. Loutfy et al., J. Chem. Phys. (1979), Vol. 71, p. 1211

Non-patent Document 2: C. W. Tang, Appl. Phys. Lett. 48 (2), 13 Jan. 1986, p. 183

Non-patent Document 3: B. Oregan, M. Gratzel, Nature, vol. 353, p. 737 (1991)

Non-patent Document 4: K. Murakoshi, R. Kogure, Y. Wada, and S. Yanagida, Chemistry Letters, 1997, p. 471

DISCLOSURE OF THE INVENTION

An object of the present invention is to provide materials for photoelectric conversion devices that have good workability and productivity and low toxicity, can be easily flexibilized, and have high photoelectric conversion efficiencies; and photoelectric conversion devices using said materials.

The present inventors, as the result of their earnest studies on photoelectric conversion devices, have found using polyacene derivatives for photoelectric conversion devices and completed the present invention.

That is, the present invention provides a material for photoelectric conversion devices composed of a polyacene derivative represented by general formula (I) below:

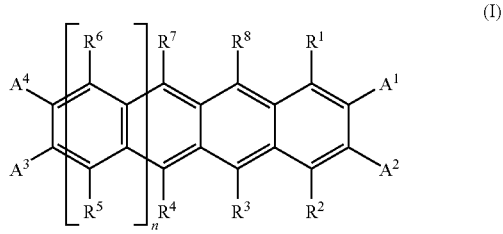

(I)

[In the formula, $R^1$, $R^2$, $R^3$, $R^4$, $R^5$, $R^6$, $R^7$, and $R^8$ are independent from each other, either the same or different, and each represents a hydrogen atom, a halogen atom, an optionally substituted hydrocarbon group having 1 to 40 carbon atoms, an optionally substituted alkoxy group having 1 to 40 carbon atoms, an optionally substituted aryloxy group having 6 to 40 carbon atoms, an optionally substituted amino group, a hydroxyl group, or an optionally substituted silyl group;

$A^1$, $A^2$, $A^3$, and $A^4$ are independent from each other, either the same or different, and each represents a hydrogen atom, a halogen atom, an optionally substituted hydrocarbon group having 1 to 40 carbon atoms, an optionally substituted alkoxy group having 1 to 40 carbon atoms, an optionally substituted aryloxy group having 6 to 40 carbon atoms; an optionally substituted alkylaryloxy group having 7 to 40 carbon atoms, an optionally substituted alkoxycarbonyl group having 2 to 40 carbon atoms, an optionally substituted aryloxycarbonyl group having 7 to 40 carbon atoms; a cyano group (—CN), a carbamoyl group (—C(=O)NH$_2$), a haloformyl group (—C(=O)—X, wherein X represents a halogen atom), a formyl group (—C(=O)—H), an isocyano group, an isocyanato group; a thiocyanato group; or a thioisocyanato group; or in each of the pair $A^1$ and $A^2$ and the pair $A^3$ and $A^4$, the groups may link to each other to form a ring represented by —C(=O)—B—C(=O)— (wherein B is an oxygen atom or a group represented by —N(B$^1$)—, and B$^1$ is a hydrogen atom, a hydrocarbon group having 1 to 40 carbon atoms or a halogen atom); or $A^3$ and $A^4$ may link to each other to form a saturated or unsaturated ring having 4 to 40 carbon atoms, and the saturated or unsaturated ring may be interrupted by an oxygen atom, a sulfur atom, or a group represented by —N(R$^{11}$)— (wherein R$^{11}$ is a hydrogen atom or a hydrocarbon group) and may have a substituent(s); and n is an integer of 1 or more].

The present invention provides, as a particularly preferred material for photoelectric conversion devices, a material for photoelectric conversion devices composed of a polyacene derivative represented by general formula (I) wherein at least one of $R^1$, $R^2$, $R^3$, $R^4$, $R^5$, $R^6$, $R^7$, $R^8$, $A^1$, $A^2$, $A^3$, and $A^4$ is not a hydrogen atom.

The present invention also provides a photoelectric conversion device comprising, between two electrodes at least one of which is light-transmitting, a layer containing one or more kinds of material for photoelectric conversion devices, the material being composed of the polyacene derivative represented by general formula (I).

The present invention also provides a photoelectric conversion device in which a layer containing an organic semiconductor is disposed between two electrodes at least one of which is light-transmitting, wherein the layer containing the organic semiconductor contains one or more kinds of material for photoelectric conversion devices, the material being composed of the polyacene derivative represented by general formula (I).

The present invention also provides a photoelectric conversion device which performs photoelectric conversion comprising a layer containing semiconductor fine particles on which a pigment is absorbed and a p-type organic semiconductor working as a hole-transporting layer disposed between two electrodes at least one of which is light-transmitting, wherein the hole-transporting layer contains one or more kinds of material for photoelectric conversion devices, the material being composed of the polyacene derivative represented by general formula (I).

The present invention also provides a photoelectric conversion device comprising a semiconductor layer(s) between two electrodes at least one of which is light-transmitting, wherein the device performs photoelectric conversion based on an organic semiconductor/metal junction, an organic semiconductor/inorganic semiconductor junction, or an organic semiconductor/organic semiconductor junction, wherein the organic semiconductor layer contains one or more kinds of material for photoelectric conversion devices, the material being composed of the polyacene derivative represented by general formula (I).

BEST MODE FOR CARRYING OUT THE INVENTION

Hereinafter, detailed explanation will be given on the materials for photoelectric conversion devices and the photoelectric conversion devices of the present invention.

The material for photoelectric conversion devices of the present invention is a polyacene derivative represented by general formula (I) above.

In general formula (I), the halogen atom represented by $R^1$, $R^2$, $R^3$, $R^4$, $R^5$, $R^6$, $R^7$, or $R^8$ includes a fluorine atom, a chlorine atom, a bromine atom, and an iodine atom.

In general formula (I), the hydrocarbon group having 1 to 40 carbon atoms (hereinafter represented as "$C_1$-$C_{40}$ hydrocarbon group"; the other groups are also represented similarly) represented by $R^1$, $R^2$, $R^3$, $R^4$, $R^5$, $R^6$, $R^7$ or $R^8$ may be either a saturated or unsaturated acyclic group or a saturated or unsaturated cyclic group. When the $C_1$-$C_{40}$ hydrocarbon group is acyclic, it may be either linear chain or branched. The $C_1$-$C_{40}$ hydrocarbon group includes a $C_1$-$C_{40}$ alkyl group, a $C_2$-$C_{40}$ alkenyl group, a $C_2$-$C_{40}$ alkynyl group, a $C_3$-$C_{40}$ allyl group, a $C_4$-$C_{40}$ alkadienyl group, a $C_4$-$C_{40}$ polyenyl group, a $C_6$-$C_{18}$ aryl group, a $C_6$-$C_{40}$ alkylaryl group, a $C_6$-$C_{40}$ aralkyl group, a $C_4$-$C_{40}$ cycloalkyl group, a $C_4$-$C_{40}$ cycloalkenyl group, and the like.

The $C_1$-$C_{40}$ alkyl group, the $C_2$-$C_{40}$ alkenyl group, the $C_2$-$C_{40}$ alkynyl group, the $C_3$-$C_{40}$ alkyl group, the $C_4$-$C_{40}$ alkadienyl group, and the $C_4$-$C_{40}$ polyenyl group are preferably a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkadienyl group, and a $C_4$-$C_{20}$ polyenyl group, respectively; and more preferably a $C_1$-$C_{10}$ alkyl group, a $C_2$-$C_{10}$ alkenyl group, a $C_2$-$C_{10}$ alkynyl group, a $C_3$-$C_{10}$ allyl group, a $C_4$-$C_{10}$ alkadienyl group, and a $C_4$-$C_{10}$ polyenyl group, respectively.

The $C_1$-$C_{40}$ hydrocarbon group may have a substituent(s).

As preferred examples of the optionally substituted $C_1$-$C_{40}$ hydrocarbon group, there may be mentioned, but not limited to, methyl, ethyl, propyl, n-butyl, t-butyl, dodecanyl, trifluoromethyl, perfluoro-n-butyl, 2,2,2-trifluoroethyl, benzyl, 2-phenoxyethyl, phenyl, 2-tolyl, 3-tolyl, 4-tolyl, naphthyl, biphenyl, 4-phenoxyphenyl, 4-fluorophenyl, 3-carbomethoxyphenyl, 4-carbomethoxyphenyl, and the like.

In general formula (I), as preferred examples of the optionally substituted $C_1$-$C_{40}$ alkoxy group represented by $R^1$, $R^2$, $R^3$, $R^4$, $R^5$, $R^6$, $R^7$, or $R^8$, there may be mentioned, but not limited to, methoxy, ethoxy, 2-methylethoxy, t-butoxy, and the like.

In general formula (I), as preferred examples of the optionally substituted $C_6$-$C_{40}$ aryloxy group represented by $R^1$, $R^2$, $R^3$, $R^4$, $R^5$, $R^6$, $R^7$, or $R^8$, there may be mentioned, but not limited to, phenoxy, naphthoxy, phenylphenoxy, 4-methylphenoxy, and the like.

In general formula (I), as preferred examples of the optionally substituted amino group represented by $R^1$, $R^2$, $R^3$, $R^4$, $R^5$, $R^6$, $R^7$, or $R^8$, there may be mentioned, but not limited to, amino, dimethylamino, methylamino, methylphenylamino, phenylamino, and the like.

In general formula (I), as the optionally substituted silyl group represented by $R^1$, $R^2$, $R^3$, $R^4$, $R^5$, $R^6$, $R^7$, or $R^8$, there may be mentioned, but not limited to, a group represented by —Si($R^{12}$)($R^{13}$)($R^{14}$) [wherein $R^{12}$, $R^{13}$, and $R^{14}$ are independent from each other and the same or different, and each represent an optionally halogenated $C_1$-$C_{40}$ alkyl group, an optionally halogenated $C_6$-$C_{40}$ aralkyl group, an optionally halogenated $C_1$-$C_{40}$ alkoxy group, or an optionally halogenated $C_6$-$C_{40}$ aralkyloxy group], and the like.

As preferred examples of the optionally substituted silyl group, there may be mentioned, but not limited to, trimethylsilyl, triethylsilyl, trimethoxysilyl, triethoxysilyl, diphenylmethylsilyl, triphenylsilyl, triphenoxysilyl, dimethylmethoxysilyl, dimethylphenoxy silyl, methylmethoxyphenylsilyl, and the like.

As the substituents that can be introduced to the $C_1$-$C_{40}$ hydrocarbon group, the $C_1$-$C_{40}$ alkoxy group, the $C_6$-$C_{40}$ aryloxy group, the amino group, or the silyl group, there may be mentioned, for example, a halogen atom, a hydroxyl group, an amino group, and the like.

The halogen atom as the above substituent includes a fluorine atom, a chlorine atom, a bromine atom, and an iodine atom. When hydrogen atom(s) in the $C_1$-$C_{40}$ hydocarbon group, the $C_1$-$C_{40}$ alkoxy group, the $C_6$-$C_{40}$ aryloxy group or the like is (are) substituted with a fluorine atom(s), the solubility of the polyacene derivative increases, and hence such a case is preferred.

In general formula (I), as the "halogen atom, optionally substituted $C_1$-$C_{40}$ hydrocarbon group, optionally substituted $C_1$-$C_{40}$ alkoxy group, and optionally substituted $C_6$-$C_{40}$ aryloxy group" represented by $A^1$, $A^2$, $A^3$, or $A^4$, there may be mentioned atoms or groups similar to the "halogen atom, optionally substituted $C_1$-$C_{40}$ hydrocarbon group, optionally substituted $C_1$-$C_{40}$ alkoxy group, and optionally substituted $C_6$-$C_{40}$ aryloxy group" represented by $R^1$, $R^2$, $R^3$, $R^4$, $R^5$, $R^6$, $R^7$, or $R^8$ described above.

In general formula (I), as preferred example of the optionally substituted $C_7$-$C_{40}$ alkylaryloxy group represented by $A^1$, $A^2$, $A^3$, or $A^4$, there may be mentioned, but not limited to, 4-methylphenoxy, 4-octylphenoxy, 4-dodecylphenoxy, 4-octadecylphenoxy, and the like.

In general formula (I), as preferred example of the optionally substituted $C_2$-$C_{40}$ alkoxycarbonyl group represented by $A^1$, $A^2$, $A^3$, or $A^4$, there may be mentioned, but not limited to, methoxycarbonyl, ethoxycarbonyl, and the like.

In general formula (I), as preferred example of the optionally substituted $C_7$-$C_{40}$ aryloxycarbonyl group represented by $A^1$, $A^2$, $A^3$, or $A^4$, there may be mentioned, but not limited to, phenoxycarbonyl, 4-methylphenoxycarbonyl, and the like.

In general formula (I), the cyano group (—CN), carbamoyl group (—C(=O)NH$_2$), haloformyl group (—C(=O)—X, wherein X represents a halogen atom), formyl group (—C(=O)—H), isocyano group, isocyanato group, thiocyanato group or isothiocyanato group represented by $A^1$, $A^2$, $A^3$, or $A^4$ can be transformed, for example, from an alkoxycarbonyl group by usual methods in organic chemistry. Further, the carbamoyl group (—C(=O)NH$_2$), haloformyl group (—C(=O)—X, wherein X represents a halogen atom), formyl group (—C(=O)—H), or the like is interconvertible with a cyano group or an alkoxycarbonyl group by usual methods in organic chemistry.

In general formula (I), in each of the pair $A^1$ and $A^2$ and the pair $A^3$ and $A^4$, the groups may link to each other to form a ring represent by —C(=O)—B—C(=O)— (wherein B is an oxygen atom or a group represented by —N($B^1$)—, and $B^1$ is a hydrogen atom, a $C_1$-$C_{40}$ hydrocarbon group or a halogen atom).

For example, when $A^1$, $A^2$, $A^3$, and $A^4$ in general formula (I) are alkoxycarbonyl groups, they can be transformed into carboxyl groups by usual methods in organic chemistry, and two adjacent carboxyl groups can be transformed into a carboxylic anhydride, that is, a ring represented by —C(=O)—O—C(=O)—, through dehydration. Further, the carboxylic anhydride can be transformed into an imide, a ring represented by —C(=O)—N($B^1$)—C(=O)—, (wherein $B^1$ has the above meaning) by usual methods in organic chemistry.

Alternatively, $A^3$ and $A^4$ in general formula (I) may link to each other to form a $C_4$-$C_{40}$ saturated or unsaturated ring. The unsaturated ring may be an aromatic ring such as a benzene ring. The ring formed by linking of $A^3$ and $A^4$ is preferably a 4- to 16-membered ring, and further preferably 4- to 12-membered ring. This ring may be either an aromatic ring or an alicyclic ring, and may be substituted with a $C_1$-$C_{20}$ hydrocarbon group, a $C_1$-$C_{20}$ alkoxy group, a $C_6$-$C_{20}$ aryloxy group, an amino group, a hydroxyl group, a silyl group, or the like.

The saturated or unsaturated ring may be interrupted by an oxygen atom, a sulfur atom, or a group represented by —N($R^{11}$)— (wherein $R^{11}$ is a hydrogen atom or a hydrocarbon group). $R^{11}$ (is preferably a hydrogen atom or a $C_1$-$C_6$ alkyl group, and further preferably a hydrogen atom or a $C_1$-$C_4$ alkyl group.

In general formula (I), n is an integer of 1 or more. Particularly in terms of the stability of the compound and the lifetime of the photoelectric conversion device, n is preferably 1 or 2. When n is 1 or 2, the polyacene derivative is tetracyclic or pentacyclic, that is, a naphthacene derivative or a pentacene derivative, respectively.

In conventional fused polycyclic aromatic compounds, the solubility tends to decrease with increase in the number of aromatic rings in said compounds. However, according to the production method described later, even if the number of aromatic rings in fused polycyclic aromatic compounds increases, solubility can be maintained by introducing various appropriate substituents. Accordingly, n is not restricted to 1 or 2 and may be an integer of 3 or more, 4 or more, or 5 or more. For example, a polyacene derivative with seven condensed benzene rings (which corresponds to n of 4) can be easily obtained.

Unsubstituted pentacene is known to have the highest carrier mobility among currently known organic compounds and is intensively studied. However, because this compound is not soluble in solvents, a vacuum vapor deposition method is typically used for forming thin films, and a wet process such as spin coating cannot be employed. Among the polyacene derivatives of the present invention represented by general formula (I), compounds wherein "at least one of $R^1$, $R^2$, $R^3$, $R^4$, $R^5$, $R^6$, $R^7$, $R^8$, $A^1$, $A^2$, $A^3$ and $A^4$ is not a hydrogen atom" can be easily designed so as to be soluble in solvents, and therefore can be formed into a thin film by spin coating or the like, resulting in a substantial improvement in workability and productivity as compared with a case where vacuum vapor deposition is used. In addition, the crystal form in the thin film can be controlled in a self-organizing manner by selecting the intramolecular and the intermolecular interactions, the type of solvent, and the like.

As a method for producing the polyacene derivatives represented by general formula (I), which are materials for photoelectric conversion devices of the present invention, there may be mentioned, for example, a method in which a fused-ring hydrocarbon represented by formula (II) below is aromatized in the presence of a dehydrogenating agent to obtain the polyacene derivative represented by general formula (I).

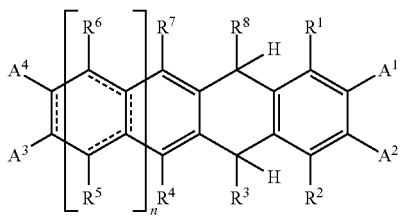
(IIa)

[In the formula, $R^1$, $R^2$, $R^3$, $R^4$, $R^5$, $R^6$, $R^7$, $R^8$, $A^1$, $A^2$, $A^3$, $A^4$, and n have the above-described meanings. The bond represented by the following symbol represents a single bond or a double bond.] ━━━

The fused-ring hydrocarbon represented by formula (II) includes, for example, fused-ring hydrocarbons represented by formulae (IIa), (IIb), and (IIc) below according to the types of the bonds.

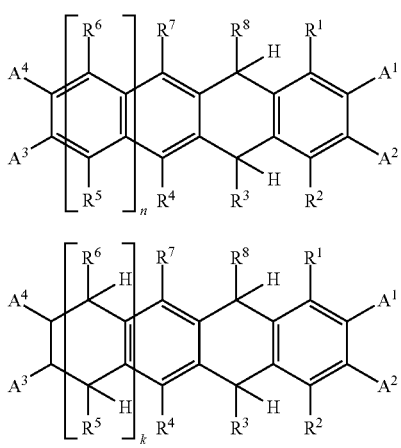

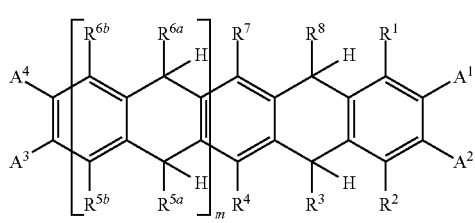

[In formulae (IIa), (IIb), and (IIc), $R^1$, $R^2$, $R^3$, $R^4$, $R^5$, $R^6$, $R^7$, $R^8$, $A^1$, $A^2$, $A^3$, $A^4$, and n have the above-described meanings. $R^{5a}$ and $R^{5b}$ each have the same meaning as $R^5$. $R^{6a}$ and $R^{6b}$ each have the same meaning as $R^6$.]

When the fused-ring hydrocarbon represented by formula (II) is a fused-ring hydrocarbon represented by formula (IIb) with n of an odd number, k in formula (IIb) is an integer represented by (n+1)/2. When the fused-ring hydrocarbon represented by formula (II) is a fused-ring hydrocarbon represented by formula (IIc) with n of an even number, m in formula (IIc) is an integer represented by n/2.

In the case of a fused-ring hydrocarbon represented by formula (IIa), one ring is to be aromatized, while in the case of a fused-ring hydrocarbon represented by formula (IIb) or (IIc), two or more rings are to be aromatized.

Note that the fused-ring hydrocarbon represented by formula (II) includes a case in which a repeating unit containing an aromatic ring and a repeating unit containing a non-aromatic ring are randomly repeated.

In the method for producing the polyacene derivative represented by general formula (I), it is preferred that the dehydrogenating agent be a combination of a lithiating agent and a de-lithiating agent and that the lithiating agent be first added to the above fused-ring hydrocarbon and subsequently the de-lithiating agent be added.

For this scheme, cases of fused-ring hydrocarbons represented by formulae (IIa), (IIb) and (IIc) will be shown below as examples.

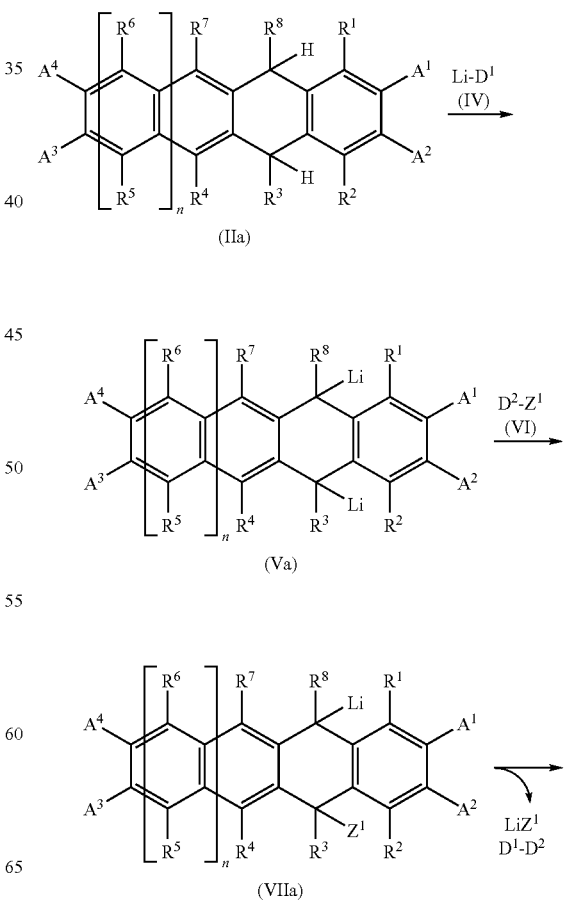

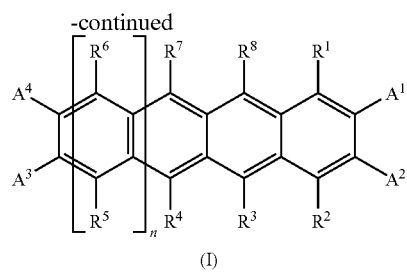

(I)

[In the formula, $R^1, R^2, R^3, R^4, R^5, R^6, R^7, R^8, A^1, A^2, A^3, A^4$, and n have the above-described meanings. $D^1$ is a nucleophilic group such as a $C_1$-$C_6$ alkyl group. $D^2$ is a $C_1$-$C_{20}$ hydrocarbon group such as a $C_1$-$C_6$ alkyl group. $Z^1$ is a leaving group such as a halogen atom.]

In this case, $R^3$ and $R^8$ in formula (IIa) are preferably hydrogen atoms in terms of ease in the synthesis of the polyacene derivative.

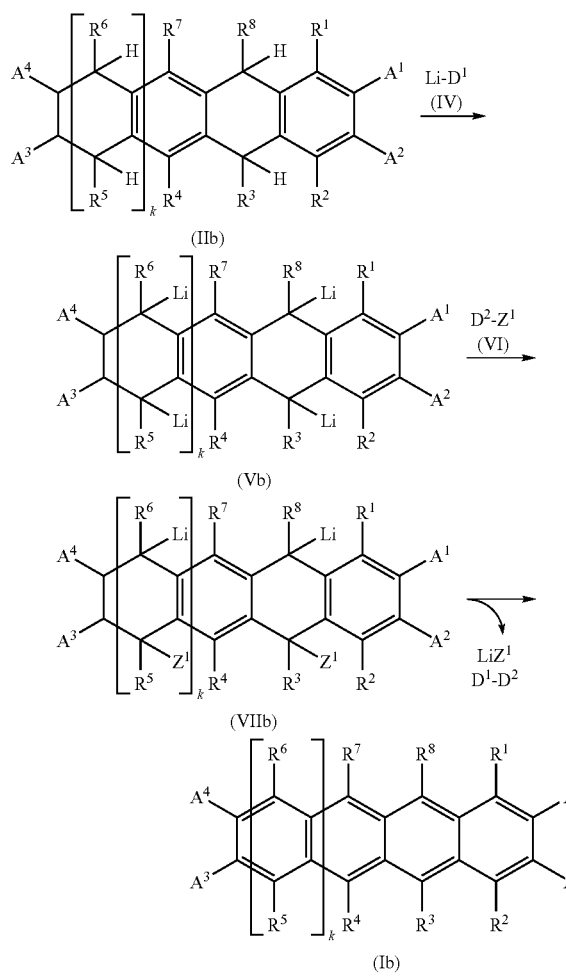

[In the formula, $R^1, R^2, R^3, R^4, R^5, R^6, R^7, R^8, A^1, A^2, A^3, A^4$, and k have the above-described meanings. $D^1$ is a nucleophilic group such as a $C_1$-$C_6$ alkyl group. $D^2$ is a $C_1$-$C_{20}$ hydrocarbon group such as a $C_1$-$C_6$ alkyl group. $Z^1$ is a leaving group such as a halogen atom.]

In this case, $R^3$, $R^5$, $R^6$, and $R^8$ in formula (IIb) are preferably hydrogen atoms in terms of ease in the synthesis of the polyacene derivative.

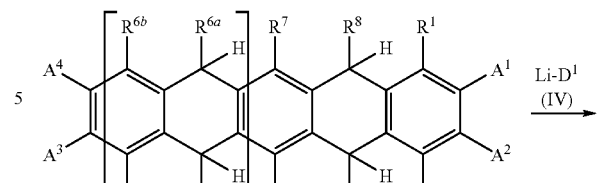

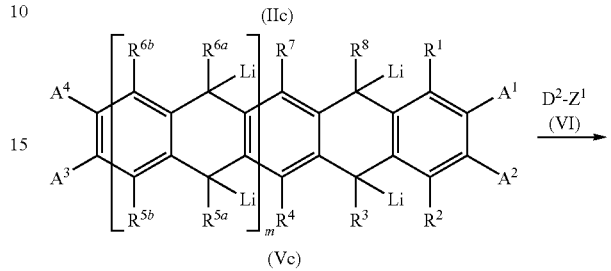

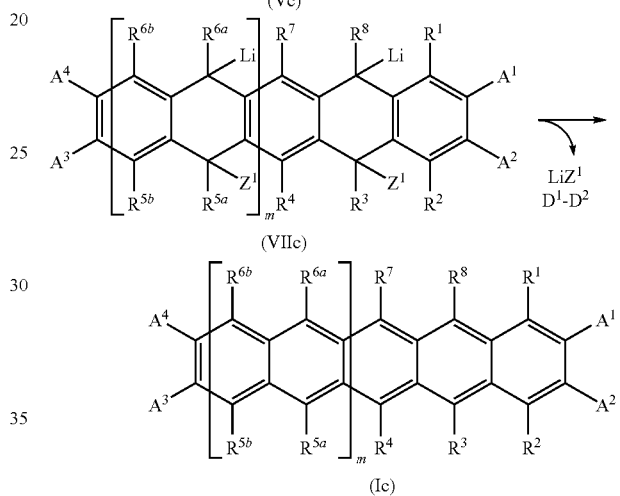

[In the formula, $R^1, R^2, R^3, R^4, R^{5a}, R^{5b}, R^{6a}, R^{6b}, R^7, R^8, A^1, A^2, A^3, A^4$, and m have the above-described meanings. $D^1$ is a nucleophilic group such as a $C_1$-$C_6$ alkyl group. $D^2$ is a $C_1$-$C_{20}$ hydrocarbon group such as a $C_1$-$C_6$ alkyl group. $Z^1$ is a leaving group such as a halogen atom.]

In this case, $R^3$, $R^{5a}$, $R^{6a}$, and $R^8$ in formula (IIc) are preferably hydrogen atoms in terms of ease in the synthesis of the polyacene derivative.

In the above schemes, for convenience in clearly showing the carbon atoms on which lithiating agent (IV) represented by Li-$D^1$ acts, a fused-ring hydrocarbon represented by formula (IIa), (IIb), or (IIc) is used. Needless to say, the combination of a lithiating agent and a de-lithiating agent can be widely applied to the fused-ring hydrocarbons represented by formula (II) as a dehydrogenating agent.

Reaction of the fused-ring hydrocarbon represented by formula (IIa), (IIb), or (IIc) with lithiating agent (IV) yields a lithiated fused-ring hydrocarbon represented by formula (Va), (Vb), or (Vc), respectively. As lithiating agent (IV), a $C_1$-$C_{20}$ lithiohydrocarbon such as an alkyllithium and an aryllithium is used preferably. For example, a $C_1$-$C_6$ alkyllithium such as butyllithium and a $C_6$-$C_{20}$ aryllithium such as phenyllithium are suitably used.

It is preferred to use an activating agent for lithiating agents together with lithiating agent (IV). The activating agent is preferably a tertiary amine; for example, N,N,N',N'-tetraalkylalkylenediamine such as N,N,N',N'-tetramethylethylenediamine (TMEDA) is used. An alkyllithium is considered to exist as an oligomer such as a tetramer in solution, and when a tertiary amine co-exists, it is considered the nitrogen atom(s) in the amine coordinate(s) to the lithium atom in the alkyllithium to destruct the oligomeric structure. Thus, the lithium atom in the alkyllithium is likely to be exposed to the solution, increasing the reactivity.

As the solvent, an organic solvent is preferred, and particularly a non-polar organic solvent is preferably used. For example, an alkane such as hexane and an aromatic compound such as benzene are preferred.

The reaction temperature is preferably 0 to 200° C., more preferably 20 to 100° C., and furthermore preferably 30 to 80° C.

Subsequently, reactions of the obtained fused-ring hydrocarbons represented by formulae (Va), (Vb), and (Vc) with a de-lithiating agent (VI) presumably yield intermediates represented by formulae (VIIa), (VIIb), and (VIIc), respectively, and these intermediates are decomposed to give polyacene derivatives represented by formulae (I), (Ib), and (Ic), respectively.

As the de-lithiating agent (VI), for example, an alkyl halide is suitably used. The alkyl halide is preferably an alkyl halide having 6 or less carbon atoms, for example, methyl iodide, ethyl bromide, and the like.

When compounds having a small number of carbon atoms are used as the lithiating agent (IV) and the de-lithiating agent (VI) in this reaction, for example, when butyllithium and methyl iodide are used as the lithiating agent (IV) and the de-lithiating agent (VI), respectively, lithium iodide and hexane are eliminated. Hexane can be removed simultaneously when the solvent is removed. Lithium iodide can be removed by washing the resultant reaction mixture with water. Accordingly, such a combination of a lithiating agent and a de-lithiating agent is preferred in terms of ease in purification of a reaction mixture.

In the method for producing the polyacene derivative represented by general formula (I), the dehydrogenating agent is preferably the compound represented by formula (III).

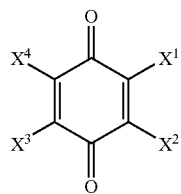

(III)

[In the formula, $X^1$, $X^2$, $X^3$, and $X^4$ are independent from each other, either the same or different, and each represents a fluorine atom or a cyano group.]

The compound represented by formula (III) reacts with the fused-ring hydrocarbon represented by formula (II) to be converted to a 1,4-dihydroxycyclohexane derivative.

The halogen atom represented by $X^1$, $X^2$, $X^3$, or $X^4$ in formula (III) is preferably a chlorine atom, a bromine atom or an iodine atom, more preferably a chlorine atom or a bromine atom, and furthermore preferably a chlorine atom.

For example, all of $X^1$, $X^2$, $X^3$ and $X^4$ may be chlorine atoms, that is, the compound represented by formula (III) may be chloranil. Alternatively, $X^1$ and $X^2$ may be cyano groups and $X^3$ and $X^4$ may be chlorine atoms, that is, the compound may be 2,3-dichloro-5,6-dicyanoquinone. All of $X^1$, $X^2$, $X^3$, and $X^4$ may be cyano groups, that is, the compound may be 1,2,5,6-tetracyanoquinone.

When the compound represented by formula (III) is used, Diels-Alder reaction of the compound represented by formula (III) and the product, polyacene derivative, may take place to generate a by-product, which is removed by column chromatography or the like, if necessary.

In order to prevent the generation of such a byproduct, the compound represented by formula (III) is used preferably in an amount of 0.9 to 1.2 equivalents, more preferably 0.9 to 1.15 equivalents, and furthermore preferably 0.95 to 1.05 equivalents with respect to the compound represented by formula (II).

As the solvent, an organic solvent is preferred, and an aromatic compound such as benzene is particularly preferred.

The reaction temperature is preferably −80 to 200° C., more preferably 0 to 100° C., and furthermore preferably 10 to 80° C. If necessary, light may be blocked during the reaction.

In the method for producing the polyacene derivative represented by formula (I), the dehydrogenating agent preferably contains palladium. For example, palladium supported on carbon such as activated carbon, which is commercially available as so-called palladium on carbon (Pd/C), can be suitably used. Pd/C is a catalyst widely used for dehydrogenation and can be applied to the present invention as in conventional cases. When Pd/C is used, the reaction temperature is, for example, 200 to 500° C., although the reaction temperature may be selected as appropriate according to conditions relating to the starting materials and other various factors.

The fused-ring hydrocarbon represented by formula (II) can be obtained, for example, by the following scheme.

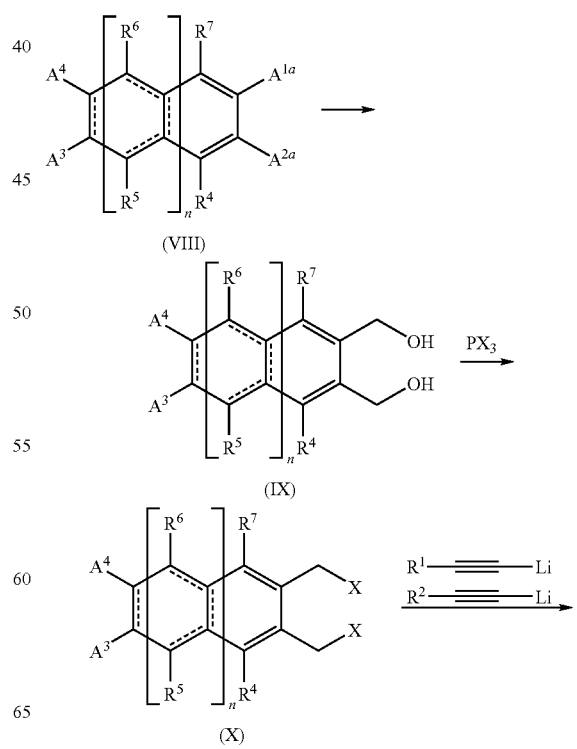

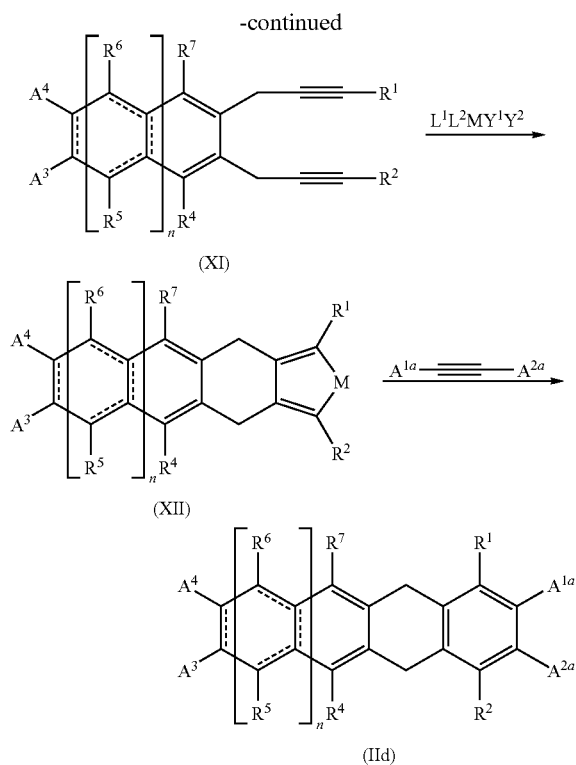

[In the formula, $R^1$, $R^2$, $R^4$, $R^5$, $R^6$, $R^7$, $A^3$, $A^4$, and n have the above-described meanings. $A^{1a}$ and $A^{2a}$ are independent from each other, either the same or different, and each represents a $C_6$-$C_{40}$ alkoxycarbonyl group optionally having a substituent containing a halogen atom(s) or a $C_6$-$C_{40}$ aryloxycarbonyl group optionally having a substituent containing a halogen atom(s). X is a leaving group such as a halogen atom. The bond represented by the following symbol represents a single bond or a double bond: ⎓

M represents a metal belonging to any of Groups 3 to 5 in the periodic table or a lanthanide metal; $L^1$ and $L^2$ are independent from each other, either the same or different, and each represents an anionic ligand, $L^1$ and $L^2$ may link to each other; and $Y^1$ and $Y^2$ are independent from each other, either the same or different, and each represents a leaving group.]

Hereinafter, the photoelectric conversion devices of the present invention will be explained. The configuration of the photoelectric conversion devices of the present invention is not particularly limited. For example, when the photoelectric conversion device is of a pn junction type, it has a structure in which a support, electrode A, a photoelectric conversion layer, electrode B, and a coating layer are sequentially laminated. In the present embodiment, electrode A is used as an electrode having the higher work function, while electrode B is used as an electrode having the lower work function. In the photoelectric conversion device, it is necessary to transmit irradiation light to the photoelectric conversion layer through at least one of electrodes A and B. In order to transmit irradiation light to the photoelectric conversion layer through the support and electrode A, the support and electrode A are formed using light-transmitting materials. Similarly, in order to transmit irradiation light to the photoelectric conversion layer through the coating layer and electrode B, the coating layer and electrode B are formed using light-transmitting materials. In order to transmit irradiation light from the both sides, the support, electrode A, electrode B, and the coating layer are formed using light-transmitting materials.

There are no particular limitations on material or thickness of the support, provided that the support can stably hold electrode A on the surface thereof. Therefore, the shape of the support may be either plate or film. As the support, for example, there are used metals such as aluminum and stainless steel, alloys thereof, plastics such as polycarbonate and polyester, wood, paper, cloth, and the like. When irradiation light is incoming from the side of support, since the support is required to be composed of a light-transmitting substance (material), glass having transparency, transparent plastics or the like may be used. Here, the term transparency means the property of transmitting light in a predetermined wavelength region used for photoelectric conversion devices, for example, light in visible region with a high transmittance. The photoelectric conversion device of the present invention is desirably formed on the surface of the support; however, when electrode A itself has certain degree of hardness and thus self-standing ability, there may be adopted a configuration in which electrode A serves also as the support, and in this case the support may be omitted.

The work function of electrode A, which has the higher work function, is preferably 4.5 V or more and more preferably 4.8 V or more in order to enable formation of a nearly ohmic junction with an organic p-type semiconducting compound contained in the photoelectric conversion layer. On the other hand, the work function of electrode B, which has the lower work function, is preferably 4.5 V or less in order to enable formation of a nearly ohmic junction with an n-type organic semiconducting compound. In the present invention, the work functions of a pair of electrodes disposed in a face-to-face arrangement may be arbitrarily selected provided that one is relatively higher than the other (that is, the work functions are different from each other). Accordingly, also for the present embodiments, it suffices that the work function of electrode A is higher than that of electrode B. In this case, the difference in work functions between the two electrodes is preferably 0.5 V or more.

As electrode A, there may be used metals such as gold, platinum, and the like; and metal oxides such as zinc oxide, indium oxide, tin oxide (NESA), tin-doped indium oxide (ITO), fluorine-doped tin oxide (FTO), and the like. On the other hand, the electrode substance used for electrode B includes, for example, lithium, lithium-indium alloy, sodium, sodium-potassium alloy, calcium, magnesium, magnesium-silver alloy, magnesium-indium alloy, indium, ruthenium, titanium, manganese, yttrium, aluminum, aluminum-lithium alloy, aluminum-calcium alloy, aluminum-magnesium alloy, graphite thin film, tin-doped indium oxide (ITO), and the like. These electrode substances may be used alone or in a combination of a plurality thereof. The electrode can be formed using these electrode substances, for example, by a vapor deposition method, a sputtering method, an ionization vapor deposition method, an ion-plating method, a cluster ion beam method, or the like. The electrodes may be formed by calcination through a sol-gel process or the like. The cathode may be either as a single-layer structure or a multi-layer structure. The thickness of electrode, which depends on the material to be used as the electrode substance, is typically set to about 5 to about 1000 nm, and more preferably about 10 to about 500 nm. At least one of the electrodes is required to be transparent or semitransparent, and it is more preferred to select the material and thickness of the electrode so that the transmittance can be 70% or more.

The photoelectric conversion layer is, for example, of pn junction type, in which at the electrode/semiconductor interfaces, the n-type semiconductor layer makes a nearly ohmic junction with electrode B which has the lower work function, and the p-type organic semiconductor layer makes a nearly ohmic junction with electrode A which has the higher work function. Accordingly, it is considered that electrons generated at the pn junction are injected into electrode B, while holes generated at the pn junction are injected into electrode A, generating a potential difference between electrodes A and B, and thereby supplying electric current outside.

In the photoelectric conversion device of the present invention, the polyacene derivative of the present invention represented by general formula (I) can work as either a p-type organic semiconducting compound or an n-type organic semiconducting compound depending on its structure. Generally, an n-type organic semiconducting compound can be obtained by introducing an electron-withdrawing functional group(s) in the polyacene skeletal structure as a substituent(s), while a p-type organic semiconducting compound can be obtained by introducing other functional group(s). Such organic semiconductors can also be obtained by doping a publicly-known compound.

The electron-withdrawing functional group includes publicly-known electron-withdrawing groups such as a carbonyl group, a cyano group, a nitro group, a sulfonyl group, a phosphonyl group, and a halo group; and functional groups bonded with these electron-withdrawing groups. Particularly, when the polyacene is used as an n-type organic semiconducting compound, it is preferred that the electron-withdrawing group is introduced in either of $A^1$, $A^2$, $A^3$, and $A^4$ in general formula (I).

The polyacene derivative of the present invention represented by general formula (I) is also suitably used as a charge-transfer material or a hole-transporting material in a charge-transfer layer or a hole-transporting layer in a dye-sensitized photoelectric conversion device.

In the photoelectric conversion device of the present invention, it is essential to use the polyacene derivative of the present invention in at least one of the photoelectric conversion layers, and publicly-known semiconducting compounds may be used in other layers. In the organic semiconductor layer using the polyacene derivative of the present invention, the polyacene derivative of the present invention may be used alone, in a combination of a plurality thereof, or in a combination with a publicly-known semiconducting compound(s).

As other p-type semiconducting compounds usable in the present invention, there may be mentioned a phthalocyanine pigment, an indigo pigment, a thioindigo pigment, a quinacridone pigment, and the like. As other compounds having hole-injecting/transporting function usable in the present invention, there may be mentioned a triarylmethane derivative, a triarylamine derivative, an oxazole derivative, a hydrazone derivative, a stilbene derivative, a pyrazoline derivative, a polysilane derivative, polyphenylenevinylene and a derivative thereof, polythiophene and a derivative thereof, a poly-N-vinylcarbazole derivative, and the like. The triarylamine derivative includes, for example, 4,4'-bis[N-phenyl-N-(4"-methylphenyl)amino]biphenyl, 4,4'-bis[N-phenyl-N-(3"-methylphenyl)amino]biphenyl, 4,4'-bis[N-phenyl-N-(3"-methoxyphenyl)amino]biphenyl, 4,4'-bis[N-phenyl-N-(1"-naphthyl)amino]biphenyl, 3,3'-dimethyl-4,4-bis[N-phenyl-N-(3"-methylphenyl)amino]biphenyl, 1,1-bis[4-[N,N-di(4"-methylphenyl)amino]phenyl]cyclohexane, 9,10-bis[N-(4-methylphenyl)-N-(4"-n-butylphenyl)amino]phenanthrene, 3,8-bis(N,N-diphenylamino)-6-phenylphenanthridine, 4-methyl-N,N-bis[4",4"'-bis[N,N-di(4-methylphenyl) amino]biphenyl-4-yl]aniline, N,N-bis[4-(diphenylamino) phenyl]-N,N-diphenyl-1,3-diaminobenzene, N,N-bis[4-(diphenylamino)phenyl]-N,N-diphenyl-1,4-diaminobenzene, 5,5"-bis[4-(bis[4-methylphenyl]amino) phenyl]-2,2:5,2"-terthiophene, 1,3,5-tris(diphenylamino) benzene, 4,4',"4"-tris(N-carbazolyl)triphenylamine, 4,4', 4"-tris[N-(3"'-methylphenyl)-N-phenylamino]triphenylamine, 4,4',4"-tris[N,N-bis(4"'-tert-butylbiphenyl-4""-yl) amino]triphenylamine, 1,3,5-tris[N-(4-diphenylaminophenyl)-N-phenylamino]benzene, and the like. The compounds having hole-injecting/transporting function may be used alone or in a combination of a plurality thereof.

As other n-type semiconducting compounds usable in the present invention, there may be used an organic compound such as a perylene pigment, a perylene pigment, a polycyclic quinone pigment, an azo pigment, $C_{60}$, $C_{70}$ fullerene, and the like; and an inorganic compound such as zinc oxide, titanium oxide, cadmium sulfide, and the like. Also, there may be used an organometallic compound [for example, tris(8-quinolinolato)aluminum, bis(10-benzo[h]quinolinolato)beryllium, beryllium salt of 5-hydroxyflavone, aluminum salt of 5-hydroxyflavone], an oxadiazole derivative [for example, 1,3-bis [5-(p-tert-butylphenyl)-1,3,4-oxadiazol-2-yl]benzene], a triazole derivative [for example, 3-(4-tert-butylphenyl)-4-phenyl-5-(4"-biphenyl)-1,2,4-triazole, a triazine derivative, a quinoline derivative, a quinoxaline derivative, a diphenylquinone derivative, a nitro-substituted fluorenone derivative, a thiopyran dioxide derivative, and the like.

The method for forming the photoelectric conversion layer is not particularly limited. For example, the photoelectric conversion layer can be produced by forming a thin film using a vacuum vapor deposition method, an ionization vapor deposition method, or a solution coating method (for example, spin-coating, casting, dip-coating, bar-coating, roll-coating, Langmuir-Blodgett method, inkjet method, etc.). When each layer is formed by a vacuum vapor deposition method, the conditions for vacuum vapor deposition are preferably, but not limited to, under vacuum at a pressure of approximately $10^{-5}$ Torr or less, a boat temperature (deposition source temperature) of about 50 to about 600° C., a substrate temperature of about −50 to about 300° C. and a deposition rate of about 0.005 to about 50 nm/sec. In this case, by forming the layers successively under vacuum, a photoelectric conversion device more excellent in various characteristics can be produced. When each layer is formed using a plurality of compounds by a vacuum vapor deposition method, it is preferred that the compounds are co-deposited while the temperature of each boat containing each compound is individually controlled.

When each layer is formed by a solution coating method, the component(s) forming each layer, or the component(s) and a binder resin or the like, are dissolved or dispersed in an appropriate organic solvent and/or water to prepare a coating solution. The usable binder resin includes, for example, a polymer such as poly-N-vinylcarbazole, polyallylate, polystyrene, polyester, polysilane, poly(methyl acrylate), poly (methyl methacrylate), polyether, polycarbonate, polyamide, polyimide, polyamideimide, poly-p-xylylene, polyethylene, polyethylene ether, polypropylene ether, polyphenylene oxide, polyether sulfone, polyaniline and a derivative thereof, polythiophene and a derivative thereof, polyphenylenevinylene and a derivative thereof, polyfluorene and a derivative thereof, polythienylenevinylene and a derivative thereof, and the like. The binder resins may be used alone or in a combination of a plurality thereof.

As the appropriate solvent used in the solution coating method, there may be mentioned, for example, a hydrocarbon solvent such as hexane, octane, decane, toluene, xylene, ethylbenzene, 1-methylnaphthalene, and the like; a ketone-type solvent such as acetone, methyl ethyl ketone, methyl isobutyl ketone, cyclohexanone, and the like; a halogenated hydrocarbon solvent such as dichloromethane, chloroform, tetrachloromethane, dichloroethane, trichloroethane, tetrachloroethane, chlorobenzene, dichlorobenzene, chlorotoluene, and the like; an ester-type solvent such as ethyl acetate, butyl acetate, amyl acetate, and the like; an alcoholic solvent such as methanol, ethanol, propanol, butanol, pentanol, hexanol, cyclohexanol, methylcellosolve, ethylcellosolve, ethylene glycol, and the like; an ethereal solvent such as dibutyl ether, tetrahydrofuran, dioxane, anisole, and the like; a polar solvent such as N,N-dimethylformamide, N,N-dimethylacetamide, 1-methyl-2-pyrrolidone, 1,3-dimethyl-2-imidazolidinone, dimethyl sulfoxide, and the like; and others. A thin film can be formed from the coating solution by various kinds of coating methods.

The method for dispersing is not particularly limited, and a dispersion containing fine particulates can be prepared, for example, using a ball mill, a sand mill, a paint shaker, an atoliter, a homogenizer, or the like. The concentration of the coating solution may be set in a range suitable for preparing a film with the desired thickness by the method to be employed without particular limitations. The concentration of the solution is typically about 0.1 to about 50 mass %, and preferably about 1 to about 30 mass %. When the binder resin is used, its amount to be used is set to, but not limited to, typically about 5 to about 99.9 mass %, preferably about 10 to about 99 mass %, and more preferably about 15 to about 90 mass % with respect to the amount of the component forming each layer (when a single-layer device is produced, with respect to the total amount of the components).

With the polyacene derivative of the present invention, molecules soluble in solvents can easily be designed, and hence a thin film can be suitably formed by the above-described solution coating methods such as spin-coating, resulting in significant improvement in workability and productivity.

The thickness (film thickness) of the photoelectric conversion layer is preferably set to, but not limited to, about 5 nm to about 5 μm in general. For the purpose of preventing contact with oxygen, moisture or the like, the produced device may be provided with a protective layer (blocking layer), or may be protected by sealing the device into an inert substance, for example, paraffin, liquid paraffin, silicone oil, fluorocarbon oil, zeolite-containing fluorocarbon oil, and the like.

The material used for the protective layer includes, for example, an organic polymer material (for example, fluororesin, epoxy resin, silicone resin, epoxysilicone resin, polystyrene, polyester, polycarbonate, polyamide, polyimide, polyamideimide, poly-p-xylylene, polyethylene, polyphenylene oxide), an inorganic material (for example, diamond thin film, amorphous silica, electric insulating glass, metal oxide, metal nitride, metal carbide, metal sulfide), photocurable resin, and the like. The materials used for the protective layer may be used alone or in a combination of a plurality thereof. The protective layer may be either a single-layer structure or a multi-layer structure.

The electrode may be provided, for example, with a metal oxide film (for example, aluminum oxide film) or a metal fluoride film as a protective film. Further, on the electrode surface, there may be provided an interface layer (intermediate layer) made of an organophosphorous compound, polysilane, an aromatic amine derivative, a phthalocyanine derivative (for example, copper phthalocyanine), or carbon. Further, the electrode may be used after the surface thereof is treated, for example, with an acid or ammonia/hydrogen peroxide or after plasma treatment.

The material for photoelectric conversion devices and the photoelectric conversion device using said material, which are related to the present invention, are suitably used for a solar cell.

EXAMPLES

Hereinafter, the present invention will be explained in more detail with reference to Examples, but the present invention is not limited to these examples.

Synthesis Example 1

Synthesis of Compound 1 of the Present Invention

Compound 1 of the present invention represented by the following formula was synthesized as follows.

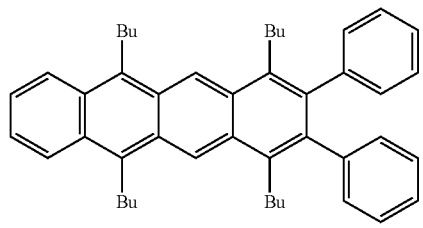

(Compound 1)

To zirconocene dichloride dissolved in THF, 2 equivalents of n-butyllithium were added at −78° C., and the resultant mixture was stirred for 1 hr. To this solution was added 1 equivalent of Diyne 1, the compound shown below, and the mixture was stirred at room temperature to generate Zirconacyclopentadiene 1, the compound shown below. To this compound were added 2 equivalents of $NiCl_2(PPh_3)_2$ complex and 1 equivalent of diphenylacetylene, and the resultant mixture was stirred at 50° C. for 3 hr to obtain dihydro-compound of Compound 1, which was reacted with 1 equivalent of 2,3-dichloro-5,6-dicyanobenzoquinone (DDQ) to obtain Compound 1 as red crystals. Compound 1 obtained here was purified by sublimation and used for evaluation of the photoelectric conversion device described below.

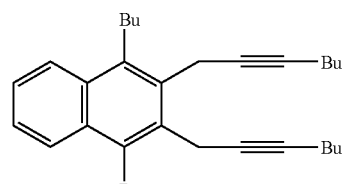

(Diyne 1)

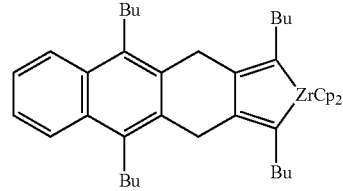

(Zirconacyclopentadiene 1)

Synthesis Example 2

Synthesis of Compound 2 of the Present Invention

Compound 2 of the present invention represented by the following formula was synthesized as follows.

(Compound 2)

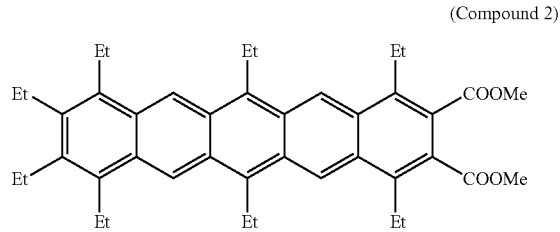

To zirconocene dichloride dissolved in THF, 2 equivalents of n-butyllithium were added at −78° C., and the resultant mixture was stirred for 1 hr. To this solution was added 1 equivalent of Diyne 2, the compound shown below, and the mixture was stirred at room temperature to generate Zirconacyclopentadiene 2, the compound below. To this compound were added 2 equivalents of CuCl, 3 equivalents of N,N-dimethylpropyleneurea (DMPU), and 1 equivalent of dimethyl acetylenedicarboxylate (DMAD), and the resultant mixture was stirred at 50° C. for 3 hr to obtain dihydro-compound of Compound 2, which was reacted with 1 equivalent of 2,3-dichloro-5,6-dicyanobenzoquinone (DDQ) to obtain Compound 2. Compound 2 obtained here was purified by sublimation and used for evaluation of the photoelectric conversion device described below.

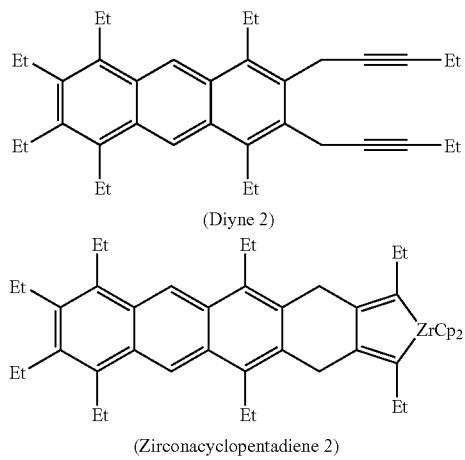

(Diyne 2)

(Zirconacyclopentadiene 2)

Synthesis Example 3

Synthesis of Compound 3 of the Present Invention

Compound 3 of the present invention represented by the following formula was synthesized as follows.

(Compound 3)

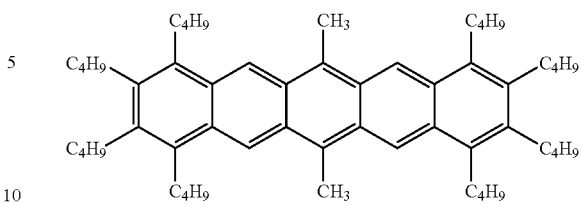

To zirconocene dichloride dissolved in THF, 2 equivalents of n-butyllithium were added at −78° C., and the resultant mixture was stirred for 1 hr. To this solution was added 0.5 equivalent of Tetrayne 3, the compound shown below, and the mixture was stirred at room temperature to generate Zirconacyclopentadiene 3, the compound below. To this compound were added 4 equivalents of $NiCl_2(PPh_3)_2$ complex and 2 equivalents of 5-decyne, and the resultant mixture was stirred at 50° C. for 3 hr to obtain tetrahydro-compound of Compound 3, which was reacted with 2 equivalents of chloranil to obtain Compound 3. Compound 3 obtained here was purified by sublimation and used for evaluation of the photoelectric conversion device described below.

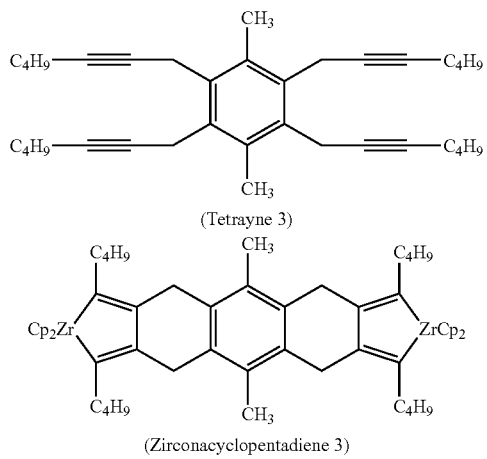

(Tetrayne 3)

(Zirconacyclopentadiene 3)

Synthesis Example 4

Synthesis of Compound 4 of the Present Invention

Compound 4 of the present invention represent by the following formula was synthesized as follows.

(Compound 4)

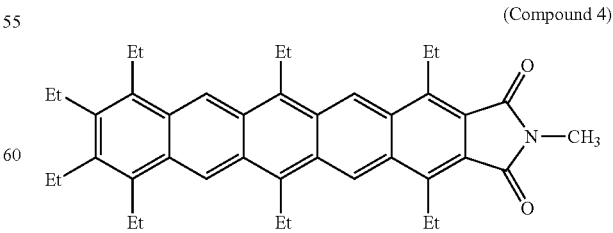

To a methanolic solution of Compound 2 obtained in Synthesis Example 2, KOH was added and the reaction was performed at 100° C. for 6 hr. The product was treated with hydrochloric acid to obtain a dicarboxylic acid. Acetic anhydride was added to this compound and the mixture was refluxed for 3 hr to obtain an acid anhydride, which was reacted with methylamine to obtain Compound 4. Compound 4 obtained here was purified by sublimation and used for evaluation of the photoelectric conversion device described below.

Synthesis Example 5

Synthesis of Compound 5 of the Present Invention

Compound 5 of the present invention represented by the following formula was synthesized as follows.

(Compound 5)

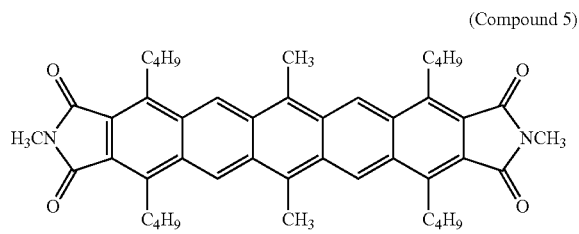

To a methanolic solution of the tetraester represented by the following formula obtained from Zirconacyclopentadine 3, KOH was added and the mixture was heated at 100° C. for 6 hr. The product was treated with hydrochloric acid to obtain a tetracarboxylic acid. Acetic anhydride was added to this compound and the mixture was refluxed for 3 hr to obtain an acid anhydride, which was reacted with methylamine to obtain Compound 5. Compound 5 obtained here was purified by sublimation and used for evaluation of the photoelectric conversion device described below.

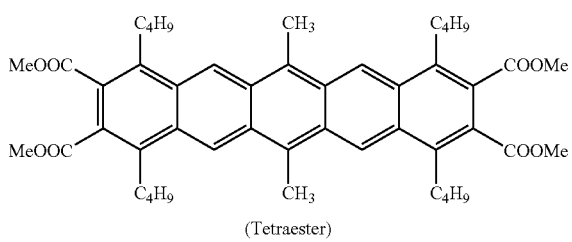

(Tetraester)

Synthesis Example 6

Synthesis of Compound 6 of the Present Invention

Compound 6 of the present invention represented by the following formula was synthesized as follows.

(Compound 6)

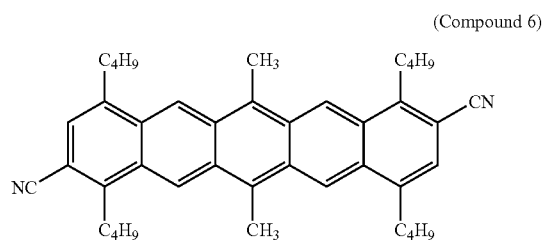

Reaction of Zirconacyclopentadiene 3 with 2 equivalents of dicyanoethylene in the presence of 2 equivalents of copper chloride and 3 equivalents of N,N-dimethylpropyleneurea (DMPU) yielded tetrahydro-compound of Compound 6, which was reacted with 2 equivalents of 2,3-dichloro-5,6-dicyanobenzoquinone (DDQ) to obtain Compound 6. Compound 6 obtained here was purified by sublimation and used for evaluation of the photoelectric conversion device described below.

The compound represented by the following formula was used as Compound 7 of the present invention.

(Compound 7)

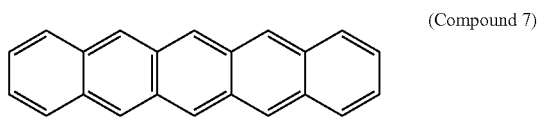

[Comparative Compounds]

The following compounds were purchased from Tokyo Chemical Industry Co., Ltd. and purified by sublimation to use as Comparative Compounds.

(Comparative Compound 1)

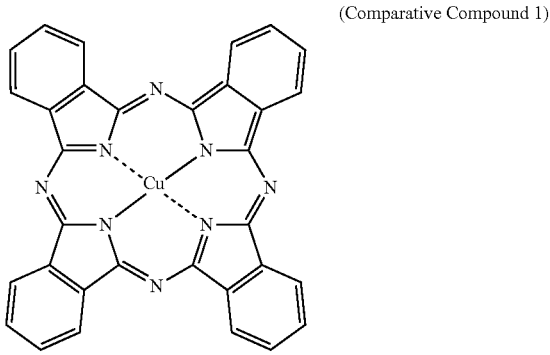

(Comparative Compound 2)

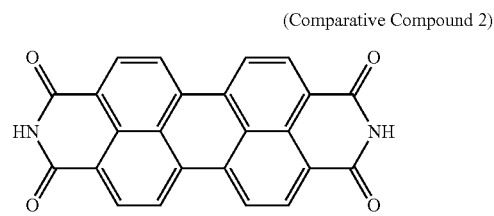

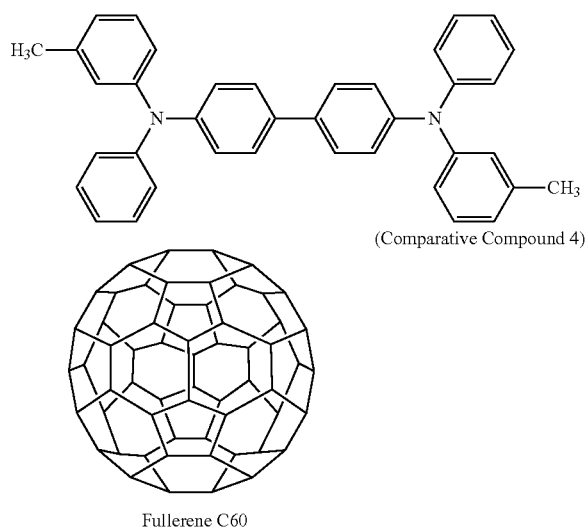

(Comparative Compound 3)

(Comparative Compound 4)

Fullerene C60

Example 1

Evaluation of Schottky Barrier Photoelectric Conversion Devices

A glass substrate equipped with an ITO transparent electrode of 130 nm in thickness was subjected to ultrasonic cleaning using acetone, substrate cleaner, distilled water, and isopropyl alcohol in this order, further subjected to UV/ozone cleaning, and then fixed on a holder of a vacuum vapor deposition apparatus. The deposition chamber was evacuated to approximately $10^{-6}$ Torr and the p-type organic semiconducting compound shown in Table 1 below was deposited on the ITO transparent electrode at a film thickness of approximately 500 nm. Subsequently, a patterned mask (light receiving area was 2 mm×2 mm) was put on the deposited film and aluminum was deposited through this mask at a film thickness of approximately 150 nm as another electrode to produce a Schottky barrier photoelectric conversion device. The characteristics of this photoelectric conversion device were evaluated with white light at an intensity of 100 mW/cm² using a photoelectric conversion device evaluation system manufactured by Bunkoh-Keiki Co., Ltd. The results are shown in Table 1.

TABLE 1

| Structure of device p-type organic semiconducting compound | Open circuit voltage (V) | Short circuit current (mA/cm²) | Fill factor | Conversion efficiency (%) |
|---|---|---|---|---|
| Example 1-1 Compound 1 | 0.61 | 0.08 | 0.40 | 0.02 |
| Example 1-2 Compound 2 | 0.63 | 0.06 | 0.44 | 0.02 |
| Example 1-3 Compound 7 | 0.60 | 0.05 | 0.38 | 0.01 |
| Comparative Example 1-1 Comparative Compound 1 | | No photovoltaic generation was observed. | | |
| Comparative Example 1-2 Comparative Compound 2 | | No photovoltaic generation was observed. | | |

Example 2

Evaluation of pn Junction Photoelectric Conversion Devices

An ITO transparent electrode was cleaned similarly to Example 1, and the p-type organic semiconducting compound shown in Table 2 below was deposited on the ITO substrate at a film thickness of approximately 50 nm, and thereon were deposited the n-type organic semiconducting compound shown in Table 2 at a film thickness of approximately 50 nm, lithium fluoride at a thickness of approximately 1 nm, and aluminum, which served as an electrode, at a thickness of approximately 150 nm in this order to produce a pn junction photoelectric conversion device. The characteristics of this photoelectric conversion device were evaluated similarly to Example 1. The results are shown in Table 2.

TABLE 2

| | Structure of device | | Results of evaluation | | | |
|---|---|---|---|---|---|---|
| | n-type organic semiconducting compound | p-type organic semiconducting compound | Open circuit voltage (V) | Short circuit current (mA/cm²) | Fill factor | Conversion efficiency (%) |
| Example 2-1 | Comparative Compound 2 | Compound 1 | 0.61 | 0.85 | 0.38 | 0.20 |
| Example 2-2 | Comparative Compound 2 | Compound 2 | 0.65 | 0.65 | 0.42 | 0.17 |
| Example 2-3 | Comparative Compound 2 | Compound 3 | 0.63 | 0.90 | 0.38 | 0.22 |
| Example 2-4 | Compound 4 | Comparative Compound 1 | 0.60 | 0.53 | 0.40 | 0.13 |
| Example 2-5 | Compound 5 | Comparative Compound 1 | 0.58 | 1.1 | 0.45 | 0.30 |
| Example 2-6 | Compound 6 | Comparative Compound 1 | 0.55 | 1.2 | 0.40 | 0.28 |
| Example 2-7 | Compound 5 | Compound 2 | 0.64 | 1.1 | 0.47 | 0.35 |
| Example 2-8 | Comparative Compound 4 | Compound 7 | 0.58 | 0.52 | 0.43 | 0.13 |
| Comparative Example 2-1 | Comparative Compound 2 | Comparative Compound 1 | 0.43 | 0.63 | 0.39 | 0.11 |

Example 3

Evaluation of pn Junction Photoelectric Conversion Devices

An ITO transparent electrode was cleaned similarly to Example 1, and the ITO substrate was coated with the solution prepared by dissolving the p-type organic semiconducting compound shown in Table 3 below in 1,2-dichloroethane, and the coating was dried to prepare a thin film having a thickness of 100 nm. Subsequently the substrate was fixed on a substrate holder of the vapor deposition apparatus, and hereinafter similarly to Example 1, there were deposited Comparative Compound 2 at a film thickness of approximately 50 nm, lithium fluoride at a thickness of approximately 1 nm, and aluminum, which served as an electrode, at a thickness of approximately 150 nm in this order to produce a pn junction photoelectric conversion device. The characteristics of this photoelectric conversion device were evaluated similarly to Example 1. The results are shown in Table 3.

TABLE 3

| | Structure of device | Results of evaluation | | | |
|---|---|---|---|---|---|
| | p-type organic semiconducting compound | Open circuit voltage (V) | Short circuit current (mA/cm$^2$) | Fill factor | Conversion efficiency (%) |
| Example 3-1 | Compound 1 | 0.60 | 0.40 | 0.25 | 0.06 |
| Example 3-2 | Compound 2 | 0.63 | 0.35 | 0.27 | 0.06 |
| Example 3-3 | Compound 7 | No thin film could be formed due to lack of solubility in solvent. | | | |
| Comparative Example 3-1 | Comparative Compound 1 | No thin film could be formed due to lack of solubility in solvent. | | | |

Example 4

Evaluation of Dye-Sensitized Photoelectric Conversion Devices

In a mixture consisting of 10 mL of 2-propanol, 380 mL of ion-exchanged water, and 3 mL of 70% nitric acid, 62.5 mL of titanium tetraisopropoxide was dissolved and hydrolyzed at 80° C. for 8 hr. The resultant solution was concentrated by evaporating solvent to prepare a stable colloid solution of titanium oxide. The particle size of titanium oxide in this colloid solution was approximately 8 nm. The surface of an ITO substrate having a thickness of 0.5 μm was spin-coated with a mixture consisting of 10 g of the above colloid solution, 2 g of TiO$_2$ fine powder (Trade name "P-25", Nippon Aerosil Co., Ltd.), and 2 g of polyethylene glycol, and then the coating was calcined at 500° C. for 1 hr to prepare a porous titanium oxide film having a thickness of 10 μm. Next, this substrate was immersed in an ethanolic solution of sensitizer dye, cis-di(thiocyanato)-N,N-bis(2,2-bipyridyl-4,4-dicarboxylic acid)ruthenium(II), and the solution was refluxed for 1 hr so that the dye was adsorbed on the substrate. Subsequently, the compound shown in Table 4 below was deposited at a film thickness of 500 nm to prepare a thin film, on which platinum was deposited at a film thickness of approximately 100 nm, which served as an electrode, to produce a dye-sensitized photoelectric conversion device. The characteristics of this photoelectric conversion device were evaluated similarly to Example 1. The results are shown in Table 4.

TABLE 4

| | Structure of device | Results of evaluation | | | |
|---|---|---|---|---|---|
| | hole-transporting layer | Open circuit voltage (V) | Short circuit current (mA/cm$^2$) | Fill factor | Conversion efficiency (%) |
| Example 4-1 | Compound 1 | 0.54 | 1.3 | 0.35 | 0.25 |
| Example 4-2 | Compound 2 | 0.52 | 1.1 | 0.37 | 0.21 |
| Comparative Example 4-1 | Comparative Compound 3 | 0.42 | 0.07 | 0.30 | 0.01 |

INDUSTRIAL APPLICABILITY

The present invention can provide materials for photoelectric conversion devices that have excellent workability and productivity, low toxicity, high photoelectric conversion efficiency and can be easily flexibilized; and photoelectric conversion devices using said materials.

What is claimed is:
1. A photoelectric conversion device of a pn junction type in a solar cell, comprising, in an arrangement adapted for use in the solar cell:
   a p-type organic semiconductor layer and an n-type organic semiconductor layer between two electrodes, at least one of said two electrodes being light transmitting,
   wherein said n-type organic semiconductor layer contains an n-type organic semiconducting compound composed of a first polyacene derivative represented by formula (I) below in which any one of $A^1$, $A^2$, $A^3$, and $A^4$ contains an electron-withdrawing functional group, and
   wherein said p-type organic semiconductor layer contains a p-type organic semiconducting compound composed of a second polyacene derivative represented by formula (I) below,

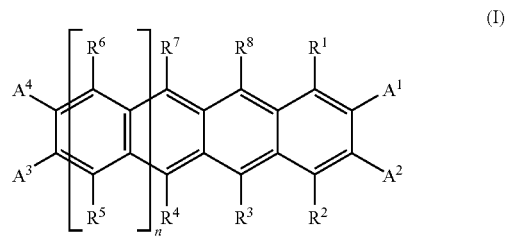

(I)

wherein $R^1$, $R^2$, $R^3$, $R^4$, $R^5$, $R^6$, $R^7$, and $R^8$ are independent from each other, either the same or different, and each represents a hydrogen atom, a halogen atom, an optionally substituted hydrocarbon group having 1 to 40 carbon atoms, an optionally substituted alkoxy group having 1 to 40 carbon atoms, an optionally substituted aryloxy group having 6 to 40 carbon atoms, an optionally substituted amino group, a hydroxyl group, or an optionally substituted silyl group;
wherein $A^1$, $A^2$, $A^3$, and $A^4$ are independent from each other, either the same or different, and each represents an optionally substituted alkoxycarbonyl group having 2 to 40 carbon atoms, an optionally substituted aryloxycarbonyl group having 7 to 40 carbon atoms, a carbamoyl group (C(=O)NH$_2$), a haloformyl group (C(=O)X, wherein X represents a halogen atom), a formyl group (C(=O)H), an isocyano group, an isocyanato group, a thiocyanato group, or a thioisocyanato group; or for each of the pair $A^1$ and $A^2$ and the pair $A^3$ and $A^4$, the groups may link to each other to form a ring represented by $C(=O)BC(=O)$, wherein B is an oxygen atom or a group represented by $N(B^1)$, $B^1$ being a hydrogen atom, a hydrocarbon group having 1 to 40 carbon atoms or a halogen atom; and wherein n is an integer of 1 or more.

2. The photoelectric conversion device of claim 1, wherein each of said first and second polyacene derivative represented by formula (I) is a polyacene derivative in which:

each of $A^1$, $A^2$, $A^3$, and $A^4$ represents an optionally substituted alkoxycarbonyl group having 2 to 40 carbon atoms, an optionally substituted aryloxycarbonyl group having 7 to 40 carbon atoms, a carbamoyl group $(C(=O)NH_2)$; or for each of the pair $A^1$ and $A^2$ and the pair $A^3$ and $A^4$, the groups may link to each other to form a ring represented by $C(=O)BC(=O)$, wherein B is an oxygen atom or a group represented by $N(B^1)$, $B^1$ being a hydrogen atom, a hydrocarbon group having 1 to 40 carbon atoms or a halogen atom.

3. The photoelectric conversion device of claim 1, wherein said second polyacene derivative represented by formula (I) is a polyacene derivative in which:

each of $A^1$, $A^2$, $A^3$, and $A^4$ represents a carbamoyl group $(C(=O)NH_2)$; or for each of the pair $A^1$ and $A^2$ and the pair $A^3$ and $A^4$, the groups may link to each other to form a ring represented by $C(=O)BC(=O)$, wherein B is an oxygen atom or a group represented by $N(B^1)$, $B^1$ being a hydrogen atom, a hydrocarbon group having 1 to 40 carbon atoms or a halogen atom.

* * * * *